United States Patent [19]

Kuszmann et al.

[11] 4,332,818
[45] Jun. 1, 1982

[54] 1,4;3,6-DIANHYDRO-2,5-DIAZIDO-2,5-DIDEOXY-HEXITOLS

[75] Inventors: Janos Kuszmann; Gabor Medgyes; Ferenc Andrasy; Pal Berzsenyi, all of Budapest, Hungary

[73] Assignee: Egyt Gyógyszervegyészeti Gyár, Budapest, Hungary

[21] Appl. No.: 242,709

[22] Filed: Mar. 11, 1981

[30] Foreign Application Priority Data

Mar. 12, 1980 [HU] Hungary ............................. 580

[51] Int. Cl.$^3$ .................... A61K 31/34; C07D 493/04
[52] U.S. Cl. ................................. 424/285; 260/349; 549/464
[58] Field of Search ..................... 260/347.8; 424/285

[56] References Cited

U.S. PATENT DOCUMENTS 2,420,519  5/1947  Brown ............................. 260/347.8
4,169,152  9/1979  Le Maistre et al. ......... 260/347.8 X

*Primary Examiner*—Richard Raymond
*Attorney, Agent, or Firm*—Karl F. Ross

[57] ABSTRACT

The invention relates to new stereoisomeric 1,4;3,6-dianhydro-2,5-diazido-2,5-dideoxy-hexitols of the Formula I.

These compounds can be prepared by
(a) reacting a hexitol derivative of the general Formula II /wherein R is a mesyl or tosyl group/ in an aqueous or anhydrous organic solvent with an alkali metal azide or ammonium azide; or
(b) mesylating or tosylating a compound of the Formula III and treating the mixed ester of the general Formula IV thus obtained /wherein R is as stated above/ with a base; or
(c) subjecting a compound of the Formula III to debenzoylation and subsequently to partial esterification and treating the compound of the general Formula V thus obtained /wherein R is as stated above/ with a base.

The new compounds of the Formula I possess valuable hypnotic properties and can be used in therapy.

FORMULAE

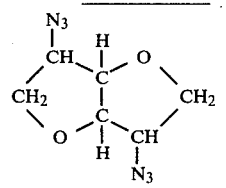

[I]

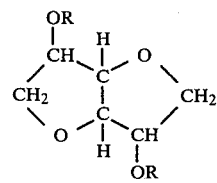

[II]

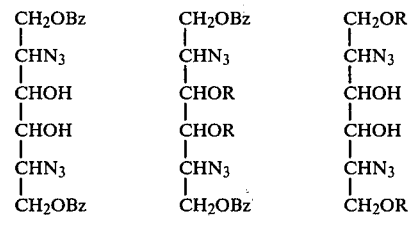

[III]  [IV]  [V]

7 Claims, No Drawings

1,4;3,6-DIANHYDRO-2,5-DIAZIDO-2,5-DIDEOXY-HEXITOLS

This invention relates to new stereoisomeric 1,4;3,6-dianhydro-2,5-diazido-2,5-dideoxy-hexitols, a process for the preparation thereof and pharmaceutical compositions containing the same.

According to a feature of the present invention there are provided new stereoisomeric 1,4;3,6-dianhydro-2,5-diazido-2,5-dideoxy-hexitols of the Formula I.

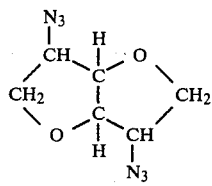

Taking into consideration the four chiral centers (C-2, C-3, C-4 and C-5) and the cis anellation of the two five-membered rings, the Formula I encompasses six compounds of different configurations (two antipodes each of mannitol, sorbitol and iditol).

The compounds of the Formula I are new, never described in prior art.

It has been found surprisingly that the compounds of the Formula I exhibit hypnotic effect of the same order of magnitude as the commercial product Glutethimid (3-ethyl-3-phenyl-2,6-dioxo-piperidine). This biological effect was unknown in the field of sugar alcohol derivatives. In the field of dianhydro hexitols only the coronary dilatatory effect of some nitric acid esters has been described—e.g. isosorbide—nitrate—[J. W. Berry, R. Carney and H. Lankford: Angiology 12, 254 (1961)].

Preferred representatives of the compounds of the Formula I are the following derivatives:
1,4;3,6-dianhydro-2,5-diazido-2,5-dideoxy-D-sorbitol;
1,4;3,6-dianhydro-2,5-diazido-2,5-dideoxy-L-iditol;
1,4;3,6-dianhydro-2,5-diazido-2,5-dideoxy-L-mannitol;
1,4;3,6-dianhydro-2,5-diazido-2,5-dideoxy-D-mannitol.

According to a further feature of the present invention there is provided a process for the preparation of new stereoisomeric 1,4;3,6-dianhydro-2,5-diazido-2,5-dideoxy-hexitols of the Formula I which comprises:

(a) reacting a hexitol derivative of the Formula II

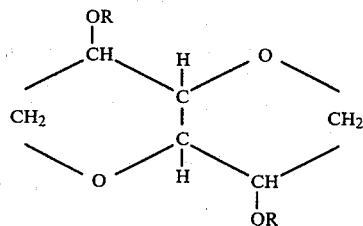

(wherein R is a mesyl or tosyl group) in an aqueous or anhydrous organic solvent with an alkali metal azide or ammonium azide; or (b) mesylating or tosylating a compound of the Formula III

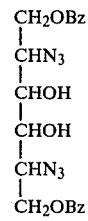

$CH_2OBz$    III
$CHN_3$
$CHOH$
$CHOH$
$CHN_3$
$CH_2OBz$ and treating the mixed ester of the Formula IV

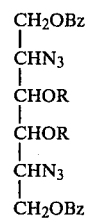

$CH_2OBz$    IV
$CHN_3$
$CHOR$
$CHOR$
$CHN_3$
$CH_2OBz$ thus obtained (wherein R is as stated above) with a base; or (c) subjecting a compound of the Formula III to debenzoylation and subsequently to partial esterification and treating the compound of the Formula V

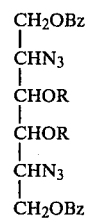

$CH_2OR$    V
$CHN_3$
$CHOH$
$CHOH$
$CHN_3$
$CH_2OR$ thus obtained (wherein R is as stated above) with a base.

The present invention is based on the recognition that the ester groups in positions 2 and 5 of the hexitol derivatives of the Formula II (wherein R is a mesyl or tosyl group) can be replaced by azido groups; and the 3,4- and 1,6-dimesyl- or -ditosyl-derivatives of the Formulae IV and V—prepared from the open-chained 2,5-diazido-1,6-dibenzoyl-2,5-dideoxy-hexitols of the Formula III—can be converted into the compounds of the Formula I by treatment with a base.

The starting materials of the Formula II are known [J. Kuszmann and G. Medgyes: Carbohydr. Res. 64, 135 (1978)]. The compounds of the Formulae III, IV and V are new and can be prepared by methods known per se. The present invention covers the new compounds of the Formulae III, IV and V and the process for their preparation as well.

What has been earlier described in connection with the stereoisomerism of the compounds of the Formula I applies to the stereoisomerism of the starting materials of the Formula II, too. The Formulae III, IV and V deal with hexitol isomers in which the carbon atoms in positions 3 and 4 are of threo configuration while carbon atoms in positions 2 and 5 may have optional configuration. Thus both compound groups cover six isomers of different configurations (two antipodes each of mannitol, sorbitol and iditol).

According to a preferred embodiment of method (a) of the process of the present invention a hexitol derivative of the Formula II is reacted in aqueous or anhydrous dimethyl formamide with sodium or ammonium azide at 120° C. or at the boiling point of the reaction mixture. After the termination of the reaction the end-product is isolated by known methods (e.g. by evaporating the filtered reaction mixture) and purified (e.g. by means of column chromatography).

According to a preferred embodiment of method (b) of the process a compound of the Formula III is reacted with an excess of mesyl chloride or tosyl chloride in pyridine as the medium at room temperature, whereupon the chloroform solution of the ester of the Formula IV thus obtained is reacted with sodium methylate in the presence of anhydrous methanol. The reaction mixture can be preferably worked up by washing with water, drying and evaporation.

The end-product can be directly purified by means of column chromatography or can be treated as follows: first the methyl benzoate is hydrolized with aqueous alkali, the end-product is extracted with chloroform, the extract is washed with water, evaporated and, if desired, subjected to column chromatography.

The ring-closure of the esters of the Formula IV can also be carried out by treating the chloroformic solution thereof with 1.1 molar equivalents of sodium methylate in the presence of methanol, washing the solution with water, evaporating the solution, admixing the residue—which contains beside methyl benzoate also the corresponding 1,4-monoanhydro derivative—with an excess of aqueous alkali. The mixture thus obtained contains the desired end-product and sodium benzoate, the end-product is extracted with chloroform, the extract is washed with water, dried and evaporated and, if necessary, purified by means of column chromatography.

According to a preferred embodiment of method (c) of the process of the present invention a compound of the Formula III is subjected to debenzoylation by treating the same in anhydrous methanol with sodium methylate, the 2,5-diazido-2,5-dideoxy-hexitol thus obtained is isolated and reacted in pyridine as medium with 2.1 to 2.3—preferably 2.2—molar equivalents of tosyl chloride or mesyl chloride and the compound of the Formula V thus obtained is converted into the end-product of the Formula I by treatment with a base—preferably by treating with sodium methylate in methanol—as described in method (b).

According to a further feature of the present invention there are provided pharmaceutical compositions comprising as active ingredient stereoisomeric 1,4;3,6-dianhydro-2,5-diazido-2,5-dideoxy-hexitol of the Formula I in admixture with suitable inert non-toxic pharmceutical carriers and optionally with pharmaceutical additives.

The pharmaceutical compositions of the present invention can be prepared by known methods of pharmaceutical industry by using the usual solid or liquid, organic or inorganic pharmaceutical carriers and auxiliary agents. The active ingredient can be finished in the form of conventional pharmaceutical formulations.

The daily dosage of the compounds of the Formula I in human therapy is preferably 200 to 500 mg for a patient having a body weight of 70 kg. The above value is but of informative character and the actual dosage may be below or above the above limits, depending on the conditions of the patient, the given situation and the prescription of the physician.

The activity of the compounds of the Formula I has been tested and compared to that of Glutethimid in various tests. The results are summarized in the following Tables. As test compound 1,4;3,6-dianhydro-2,5-diazido-2,5-dideoxy-L-mannitol is used.

In Table I the $LD_{50}$ and $HD_{50}$ values measured on mice are disclosed (HD=hypnotic dose). Table II contains the minimal hypnotic doses measured on various animals ($HD_{min}$), while in Table III the results of various CNS tests on mice are summarized.

TABLE I

| | $LD_{50}$ and $HD_{50}$ values on mice, in mg/kg | | |
|---|---|---|---|
| Test compound | Form of administration | $LD_{50}$ | $HD_{50}$ |
| 3-Ethyl-3-phenyl-2,6-dioxo-piperidine (Glutethimid) | i.p. | 305 | 135 |
| | p.o. | 580 | 200 |
| 1,4;3,6-Dianhydro-2,5-diazido-2,5-dideoxy-L-mannitol | i.p. | 380 | 195 |
| | p.o. | 390 | 220 |

TABLE II

| | Minimal hypnotic doses ($HD_{min}$) in mg/kg on various animals | |
|---|---|---|
| Animal (i.p.) | 3-Ethyl-3-phenyl-2,6-dioxo-piperidine (Glutethimid) | 1,4;3,6-Dianhydro-2,5-diazido-2,5-dideoxy-L-mannitol |
| Mouse | 100 | 100 |
| Rat | 100 | 75 |
| Cat | 125 | 175 |
| Rabbit | 175 | 125 |

TABLE III

| | Activity in CNS tests, in mg/kg, on mice | |
|---|---|---|
| Test | 3-Ethyl-3-phenyl-2,6-dioxo-piperidine (Glutethimid) | 1,4;3,6-Dianhydro-2,5-diazido-2,5-dideoxy-L-mannitol |
| Motility p.o. $ED_{50}$ | 135 | 80 |
| Tranquillizing effect (fighting test) p.o. $ED_{50}$ | 40 | 27 |
| Narcosis potentiating p.o. $ED_{100}$ | 30 | 25 |
| Rotating rod i.p. $ED_{50}$ | 70 | 68 |

The advantage of the compounds of the Formula I over the known 3-ethyl-3-phenyl-2,6-dioxo-piperidine is that the ataxical sedated state observed after the wakening of the animals comes to an end much sooner.

Further details of the present invention can be found in the following Examples, without limiting our invention to the Examples.

In the Examples Kieselgel (Geduran SI 60; manufacturer Merck) is used as absorbent in column chromatography. For the purposes of thin layer chromatography Kieselgel G (manufacturer Reanal) is used.

The following solvent mixtures are used in the column chromatography methods (the number of the solvent mixture is given as the upper index of the Rf value);

1 = 1:1 mixture of ethyl acetate and carbon tetrachloride;
2 = 1:2 mixture of ethyl acetate and carbon tetrachloride;
3 = 1:3 mixture of ethyl acetate and carbon tetrachloride;

4 = 1:5 mixture of ethyl acetate and carbon tetrachloride;

5 = 5:1 mixture of ethyl acetate and carbon tetrachloride.

The terms "mesyl" and "tosyl" used throughout the specification are the abbreviations of the methanesulphonyl and p-toluene-sulphonyl groups, respectively. (Bz=benzoyl)

EXAMPLE 1

Preparation of
1,4;3,6-dianhydro-2,5-diazido-2,5-dideoxy-D-sorbitol
(Formula I, D-sorbitol)

45 g of 1,4;3,6-dianhydro-2,5-dimesyl-D-sorbitol (Formula II, R=mesyl, D-sorbitol) or 67.7 g of of 1,4;3,6-dianhydro-2,5-ditosyl-D-sorbitol (Formula II, R=tosyl, D-sorbitol) [Carbohydr. Res. 64, 135 (1978)] are dissolved in 1.5 l of anhydrous dimethyl formamide and to the solution 30 g sodium azide are added under stirring. The suspension is heated to boiling for 4.5 hours under stirring, whereupon it is cooled and the precipitated salts are filtered off. The filtrate is evaporated, the residue is dissolved in 300 ml of chloroform, the precipitated salts are removed by filtration, the filtrate is washed with water, dried over anhydrous sodium sulfate and evaporated. The crude diazide thus obtained is purified by column chromatography under using a 1:5 mixture of ethyl acetate and carbon tetrachloride as eluent.

The fractions which contain the substance having an $R_f^4$ value of 0.40 are evaporated.

Thus 23 g of the named compound are obtained; yield 79%.

$[\alpha]_D^{20} = +170°$ (c=1, chloroform).

Analysis: for the formula $C_6H_8N_6O_2$ (molecular weight 196.14) calc.: C%=36.73; H%=4.11; N%=42.84; found: C%=36.89; H%=4.21; N%=42.63.

EXAMPLE 2

Preparation of
1,4;3,6-dianhydro-2,5-diazido-2,5-dideoxy-L-iditol
(Formula I, L-iditol)

45 g of 1,4;3,6-dianhydro-2,5-dimesyl-D-mannitol (Formula II, R=mesyl, D-mannitol) or 67.7 g of 1,4;3,6-dianhydro-2,5-ditosyl-D-mannitol (Formula II, R=Ts; D-mannitol) [Carbohydr. Res. 64, 135 (1978)] are dissolved in 1.5 l of anhydrous dimethyl formamide and to the solution 30 g of sodium azide are added under stirring. The suspension is stirred at 120° C. for 2 hours, whereupon the reaction mixture is worked up as described in Example 1. The crude product is purified by column chromatography. Thus 25 g of the named compound are obtained as a slightly yellow liquid. Yield 86%.

$[\alpha]_D^{20} = +111°$ (c=1, chloroform) $R_f^4=0.40$.

Analysis: for the formula $C_6H_8N_6O_2$ (molecular weight 196.14) calc. C%=36.73; H%=4.11; N%=42.84; found: C%=36.86; H%=4.19; N%=42.48.

EXAMPLE 3

Preparation of
1,4;3,6-dianhydro-2,5-diazido-2,5-dideoxy-L-iditol
(Formula I, L-iditol)

One proceeds according to Example 1 except that dimethyl formamide containing 10% of water is used as solvent. Thus 22.5 g of a product identical with that of Example 2 are obtained. Yield 77.4%.

EXAMPLE 4

Preparation of
1,4;3,6-dianhydro-2,5-diazido-2,5-dideoxy-L-mannitol
(Formula I, L-mannitol)

66 g of 2,5-diazido-1,6-dibenzoyl-2,5-dideoxy-L-iditol are dissolved in 150 ml of anhydrous pyridine and 30 ml of mesyl chloride are added dropwise under stirring at +10° C. within 30 minutes. The reaction mixture is allowed to stand at room temperatur for 4 hours, whereupon it is poured into icecold water. The product is extracted with chloroform, the united chloroform extracts are washed subsequently with 1 N sulfuric acid, water, a 5% aqueous sodium hydrogen carbonate solution and water and the organic layer is dried over anhydrous sodium sulfate. The solution—which contains as main product the 3,4-dimesyl derivative (Formula IV, L-iditol, R=mesyl, $R_f^3=0.60$)—is filtered and the filtrate is evaporated to 500 ml. To this solution 100 ml of a 4.65 N sodium methylate solution in methanol is added, while the temperature is raised to 40°-45° C. The reaction mixture is kept at this temperature under slight warming for a further hour, whereupon it is cooled, washed with water, dried over anhydrous sodium sulfate and evaporated. The residue contains beside the named compound ($R_F^3=0.60$) also methyl benzoate ($R_F^3=0.95$) and a contaminating component ($R_F^3=0.1$). These impurities are removed by column chromatography; as eluent a 1:1 mixture of ethyl acetate and carbon tetrachloride is used. After evaporation the aimed compound is obtained as a faint yellow liquid; yield 16.9 g/57.5%/. $[\alpha]_D^{20} = -343°$ (c=0.5, chloroform).

Analysis for the formula $C_6H_8N_6O_2$ (molecular weight 196.14): calc.: C%=36.73; H%=4.11; N%=42.84; found: C%=36.52; H%=4.00; N%=42.56.

The above starting material is prepared as follows:

Step a

Preparation of
2,5-diazido-1,6-dibenzoyl-2,5-dideoxy-3,4-isopropylidene-L-iditol 74 g 1,6-dibenzoyl-3,4-isopropylidene-2,5-ditosyl-D-mannitol [P. Brigl., H. Grüner: Chem. Bev. 67, 1969–1973 (1934)] are dissolved in 800 ml of dimethyl formamide, whereupon 16 g of sodium azide are added and the suspension is stirred at 125° C. for an hour. The clear solution thus obtained is evaporated, the residue is dissolved in chloroform, washed with water, dried over anhydrous sodium sulfate and evaporated. Thus 45.3 g of the crude 2,5-diazide are obtained, yield 94.5%. This product can be used in the following step without further purification, $[\alpha]_D^{20} = +13°$ (c=1, chloroform), $R_F^4=0.80$.

Step b

Preparation of
2,5-diazido-1,6-dibenzoyl-2,5-dideoxy-L-iditol
(Formula III, L-iditol)

The crude product obtained in step a is dissolved in 1 l of glacial acetic acid, 200 ml of 1 N hydrochloric acid are added and the reaction mixture is kept on a water bath for 30 minutes. To the cooled solution 800 of ice are added, the precipitated crystals are filtered off after further cooling, washed with 50% aqueous acetic acid and water and dried.

Yield 121 g (70%), m.p.: 128°–130° C., $[\alpha]_D^{20} = -10.7°$ (c=1, chloroform), $R_F{}^3 = 0.35$.

EXAMPLE 5

Preparation of 1,4;3,6-dianhydro-2,5-diazido-2,5-dideoxy-D-mannitol (Formula I, D-mannitol)

67 g of 2,5-diazido-2,5-dideoxy-1,6-dibenzoyl-D-mannitol are dissolved in 1 l of anhydrous methanol, whereupon the solution is made alkaline in the presence of phenolphtaleine indicator by adding a 4.5 N methanolic sodium methylate solution. The reaction mixture is heated at 50° C. until the thin layer chromatogram contains only the spot of the named compound ($R_f{}^5 = 0.30$) while the spots of the starting material ($R_f{}^5 = 0.95$) and that of the intermediate monobenzoate ($R_f{}^5 = 0.85$) can be no more detected. The cooled solution is neutralized with carbon dioxide and evaporated. The residue is dissolved in water, the methyl benzoate formed in the reaction is removed by extraction with chloroform. The aqueous layer is evaporated, the residue is dried over anhydrous sodium sulfate, filtered and evaporated. The residue is suspended in a small amount of ethyl acetate and filtered. Thus 30 g of pure 2,5-diazido-2,5-dideoxy-D-mannitol are obtained, yield 85%. M.p.: 98°–100° C., $[\alpha]_D^{20} = -38.5°$ (c=1, water), $R_f{}^5 = 0.30$.

25.2 g of the diazide thus obtained are dissolved in 150 ml pyridine, whereupon 40 g of tosyl chloride are added in small portions at +5° C. within 30 minutes under stirring. The solution is allowed to stand at room temperature overnight, poured into water and extracted with chloroform. The chloroform solution is washed subsequently with 1 N sulfuric acid, water, a 5% aqueous sodium hydrogen carbonate solution and water and dried over anhydrous sodium sulfate. The organic phase—which contains as main product the 1,6-ditosyl derivative (Formula V, R=tosyl, D-mannitol, $R_F{}^2 = 0.5$)—is filtered, evaporated to 300 ml and 50 ml of a N methanolic sodium methylate solution are added. The reaction mixture is allowed to stand at room temperature for an hour, washed with water, dried over sodium sulfate, filtered and evaporated. The residue is purified by column chromatography by using a 1:3 mixture of ethyl acetate and carbon tetrachloride as eluent. The fractions showing an $R_f{}^3$ value of 0.6 are evaporated and the residue is extracted with carbon tetrachloride. Thus 7.65 g of the pure aimed compound are obtained, yield 39%, $[\alpha]_D^{20} = +338°$ (c=1, chloroform).

Analysis: for the formula $C_6H_8N_6O_2$ (molecular weight 196.14) calc.: C%=36.73; H%=4.11; N%=42.84; found: C%=36.59; H%=4.00; N%=42.73.

The starting material used in this Example can be prepared as follows:

Step a 1,6-Dibenzoyl-3,4-isopropylidene-L-iditol 74 g of 1,2;5,6-dianhydro-3,4-isopropylidene-L-iditol [L. Varga, E. Kasztreiner: Chem. Ber. 92, 2506–2515 (1959)] are dissolved in 2 l of anhydrous dimethyl formamide, whereupon 100 g of benzoic acid and 60 g of sodium benzoate are added under stirring. The reaction mixture is stirred at 120° C. for 4 hours, whereupon it is cooled, filtered and the filtrate is evaporated. The residue is dissolved in ether and washed with a 5% aqueous sodium hydrogen carbonate solution and water, dried over anhydrous sodium sulfate, filtered and evaporated. The residue is purified by column chromatography under using a 1:1 mixture of ethyl acetate and carbon tetrachloride as eluent. The fractions showing a $R_F{}^1$ value of 0.85 are evaporated and the crude product thus obtained is recrystallized from a mixture of ether and petrolether. Thus 94 g of the pure compound named are obtained, yield 55%. M.p.: 89°–91° C., $[\alpha]_D^{20} = +8.8°$ (c=1, chloroform).

Step b 1,6-Dibenzoyl-3,4-isopropylidene-2,5-ditosyl-L-iditol 94 g of the product prepared according to step a are dissolved in 500 ml of anhydrous pyridine, whereupon at room temperature 130 g of tosyl chloride are added. The reaction mixture is allowed to stand at room temperature for 4 days, whereupon it is poured into water and the separated oil is extracted with ethyl acetate. The united organic extracts are washed subsequently with 1 N sulfuric acid, water, a 5% aqueous sodium hydrogen carbonate solution and water, dried over anhydrous sodium sulfate, filtered and evaporated. Thus 147 g of the named compound are obtained; yield 90%. This product can be used—in the next step—without further purification.

$[\alpha]_D^{20} = -67°$ (c=1, chloroform), $R_f{}^3 = 0.85$.

Step c

Preparation of 2,5-diazido-2,5-dideoxy-1,6-dibenzoyl-3,4-isopropylidene-D-mannitol 147 g of the tosylate obtained in the previous step are dissolved in 1 l of dimethyl formamide, whereupon 35 g of sodium azide are added to the solution under stirring. The reaction mixture is stirred at 120° C. for an hour, cooled and evaporated. The residue is extracted with ethyl acetate, the organic layer is washed with water, dried over anhydrous sodium sulfate and evaporated. The residue is recrystallized from methanol. Thus 85.5 g of the pure aimed compound are obtained, yield 88%, m.p.: 72°–74° C., $[\alpha]_D^{20} = +37.6°$ (c=1, chloroform), $R_F{}^4 = 0.85$.

Step d 2,5-diazido-2,5-dideoxy-1,6-dibenzoyl-D-mannitol (III, D-mannitol)

85 g of the isopropylidene derivative obtained in the previous step are dissolved in 400 ml of glacial acetic acid, whereupon 80 ml of 1 N hydrochloric acid are added. The reaction mixture is warmed on a water bath for 30 minutes and allowed to stand at room temperature for further two hours. After cooling the precipitated crystals are filtered off, washed with cold acetic acid and water and dried over potassium hydroxide. Thus 67 g of the title compound are obtained, yield 85%. After recrystallization from benzene the product melts at 189°–191° C.

$[\alpha]_D^{20} = -17°$ (c=1, pyridine), $R_F{}^3 = 0.5$.

EXAMPLE 6

Preparation of
1,4;3,6-dianhydro-2,5-diazido-2,5-dideoxy-L-mannitol
(Formula I, L-mannitol)

66 g of 2,5-diazido-1,6-dibenzoyl-2,5-dideoxy-L-iditol are dissolved in 200 ml of anhydrous methylene chloride, whereupon 55 ml of triethylamine and thereafter 30 ml of mesyl chloride are added dropwise at +10° C. within 30 minutes under stirring. The reaction mixture is allowed to stand at room temperature for 4 hours, whereupon 200 ml of chloroform are added and the mixture is washed subsequently with water, 1 N sulfuric acid, water, a 5% aqueous sodium hydrogen carbonate solution and water and dried over anhydrous sodium sulfate. The reaction mixture is further worked up as described in Example 4. Thus 18.6 g of the named compound are obtained, yield 63.2%. This product is identical with the compound prepared according to Example 4.

EXAMPLE 7

Preparation of
1,4;3,6-dianhydro-2,5-diazido-2,5-dideoxy-L-mannitol
(Formula I, L-mannitol)

Step a 1,4-anhydro-2,5-diazido-2,5-dideoxy-3-mesyl-L-altritol 66 g of 2,5-diazido-2,5-dideoxy-1,6-dibenzoyl-L-iditol are dissolved in 150 ml of anhydrous pyridine, whereupon 30 ml of mesyl chloride are added dropwise at +10° C. under stirring within 30 minutes. The reaction mixture is allowed to stand at room temperature for 4 hours and poured into icecold water. The product is extracted with chloroform, the united chloroform extracts are washed subsequently with 1 N sulfuric acid, water, a 5% aqueous sodium hydrogen carbonate solution and water, dried over anhydrous sodium sulfate and dried. The organic phase—which contains as main product the 3,4-dimesyl derivative (Formula IV, R=mesyl, L-iditol, $R_F{}^3=0.60$)—is filtered and the filtrate is evaporated to 400 ml. To the residue 40 ml of a 4 N methanolic sodium methylate solution are added, while keeping the temperature at 10°–15° C. The reaction mixture is kept at this temperature for a further hour under slight cooling, washed with water, dried over anhydrous sodium sulfate and evaporated. The residue contains beside the named compound ($R_F{}^1=0.55$) also methyl benzoate ($R_F{}^1=0.95$) from which the desired product can be freed by means of column chromatography by using a 1:1 mixture of ethyl acetate and carbon tetrachloride as eluent. The eluate is evaporated and the residue crystallized from benzene. Thus 34 g of the named compound are obtained, yield 77%. $[\alpha]_D{}^{20}=-12°$ (c=1, chloroform).

Analysis: for the formula $C_7H_{12}N_6O_5S$ (molecular weight 295.28) calc.: C%=29.49; H%=4.10; N%=28.46; S%=10.86; found: C%=29.38; H%=3.99; N%=28.37; S%=10.98.

Step b

Preparation of
1,4;3,6-dianhydro-2,5-diazido-2,5-dideoxy-L-mannitol
(Formula I, L-mannitol)

29.5 g of the 1,4-dianhydro-2,5-diazido-2,5-dideoxy-3-mesyl-L-altritol obtained in step a are dissolved in 400 ml of chloroform, whereupon 40 ml of a 4 N methanolic sodium methylate solution are added under stirring, while the temperature is kept between 40° and 44° C. The reaction mixture is kept at this temperature for a further hour under slight warming, washed with water, dried over anhydrous sodium sulfate and evaporated in vacuo. Thus 13 g of the aimed compound are obtained, yield 82%. The product is identical with the compound obtained according to Example 4.

EXAMPLE 8

Preparation of
1,4;3,6-dianhydro-2,5-diazido-2,5-dideoxy-L-mannitol
(Formula I, L-mannitol)

One proceeds according to Example 4 except that the purification of the named compound is carried out in a different way. The chloroform solution is evaporated, the residual crude product—which contains beside the named compound ($R_F{}^3=0.60$) also methyl benzoate ($R_F{}^3=0.95$) and a contamination ($R_F{}^3=0.1$)—is stirred in a solution of 70 ml of methanol, 25 g of sodium hydroxide and 400 ml of water for 4 hours. During this time the hydrolysis of the methyl benzoate takes place. The reaction mixture is extracted twice with 200 ml of chloroform each, the chloroform solution is washed with water, dried over anhydrous sodium sulfate and evaporated. The residue contains beside the named compound ($R_F{}^3=0.60$) only one impurity ($R_F{}^3=0.1$) which can be removed by means of column chromatography by using a 1:3 mixture of ethyl acetate and carbon tetrachloride as eluent. After evaporation the named compound is obtained as a faint yellow liquid. Yield 15 g (51%). The product is identical with that obtained according to Example 4.

EXAMPLE 9

Preparation of
1,4;3,6-dianhydro-2,5-diazido-2,5-dideoxy-L-mannitol
(Formula I, L-mannitol)

66 g of 2,5-diazido-2,5-dideoxy-1,6-dibenzoyl-L-iditol are dissolved in 150 ml of anhydrous pyridine, whereupon 30 ml of mesyl chloride are added dropwise at +10° C. within 30 minutes under stirring. The reaction mixture is allowed to stand at room temperature for 4 hours and poured onto icecold water. The product is extracted with chloroform, the united chloroform extracts are washed subsequently with 1 N sulfuric acid, water, a 5% sodium hydrogen carbonate solution and water and dried over anhydrous sodium sulfate. The organic phase—which contains as main product the 3,4-dimesyl derivative (Formula IV, L-iditol, R-mesyl, $R_F{}^3=0.60$)—is filtered and evaporated to 400 ml. To the residual solution 40 ml of a 4 N methanolic sodium methylate solution are added, while the temperature is kept between 10° and 15° C. The reaction mixture is stirred at this temperature for a further hour under slight cooling and stirring, whereupon it is washed with water and the organic phase is evaporated. The residue—which contains in addition to the 1,4-dianhydro-2,5-diazido-2,5-dideoxy-3-mesyl-L-altritol ($R_F{}^1=0.55$) also methyl benzoate ($R_F{}^1=0.95$)—is stirred with a solution of 60 g of sodium hydroxide and 750 ml of water at room temperature for 6 hours. The reaction mixture is extracted twice with 200 ml of chloroform each, the chloroform extracts are washed with water, dried over anhydrous aodium sulfate, evaporated and sucked in vacuo until free from solvent.

Thus 17.8 g of the named compound are obtained, yield 60.5%. This product is identical with the compound prepared according to Example 4.

EXAMPLE 10

Preparation of a pharmaceutical composition 250 mg of 1,4;3,6-dianhydro-2,5-diazido-2,5-dideoxy-L-mannitol are filled into a semihard gelatine capsule.

What is claimed is:

1. A stereoisomeric 1,4;3,6-dianhydro-2,5-diazido-2,5-dideoxy-hexitol of the Formula

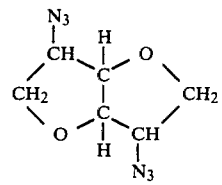

I

2. A compound according to claim 1 which is 1,4;3,6-dianhydro-2,5-diazido-2,5-dideoxy-D-sorbitol.
3. A compound according to claim 1 which is 1,4;3,6-dianhydro-2,5-diazido-2,5-dideoxy-L-iditol.
4. A compound according to claim 1 which is 1,4;3,6-dianhydro-2,5-diazido-2,5-dideoxy-L-mannitol.
5. A compound according to claim 1 which is 1,4;3,6-dianhydro-2,5-diazido-2,5-dideoxy-D-mannitol.
6. A pharmaceutical composition comprising a compound as defined in claim 1 in admixture with a pharmaceutical carrier.
7. A hypnotic method of treatment which comprises administering to a suitable subject an effective amount of a compound as defined in claim 1.

* * * * *